United States Patent [19]

Uto et al.

[11] Patent Number: 4,676,637

[45] Date of Patent: Jun. 30, 1987

[54] EXPOSURE APPARATUS WITH FOREIGN PARTICLE DETECTOR

[75] Inventors: Sachio Uto; Masataka Shiba, both of Yokohama; Yoshitada Oshida, Fujisawa, all of Japan

[73] Assignee: Hitachi, Ltd., Tokyo, Japan

[21] Appl. No.: 790,475

[22] Filed: Oct. 23, 1985

[30] Foreign Application Priority Data

Oct. 24, 1984 [JP] Japan .................................. 59-222011

[51] Int. Cl.[4] ............................................. G01N 21/00
[52] U.S. Cl. ...................................... 356/237; 356/400
[58] Field of Search ................ 356/138, 152, 153, 400, 356/401, 237; 350/582, 587; 250/491.1

[56] References Cited

U.S. PATENT DOCUMENTS 4,153,371 5/1979 Koizumi et al. ...................... 356/400
4,362,389 12/1982 Koizumi et al. ...................... 356/401

FOREIGN PATENT DOCUMENTS 59-82727 12/1984 Japan .

Primary Examiner—Eugene R. LaRoche
Assistant Examiner—Robert J. Pascal
Attorney, Agent, or Firm—Antonelli, Terry & Wands

[57] ABSTRACT

A plurality of substrate assemblies each including a substrate such as a reticle or photomask used for exposure and frames, mounted to the opposite surfaces of the substrate, to which foreign particle deposition preventive films are applied are stored in a magazine. By using a transport unit, a substrate assembly is taken out of the magazine, transported from the magazine to a mask table disposed at an exposure position and set at the mask table. A foreign particle detector is provided near the transport unit to optically detect foreign particles present on the foreign particle deposition preventive film of the substrate assembly. The substrate assembly set at the mask table is aligned to a wafer. A light beam is irradiated on the substrate assembly aligned relative to the wafer and a circuit pattern formed on the substrate is projected upon the wafer through a projection optical system to expose the wafer to the light beam through the circuit pattern.

9 Claims, 13 Drawing Figures

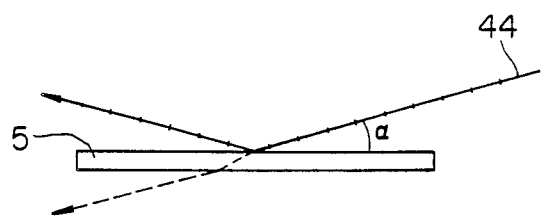
FIG. 9A
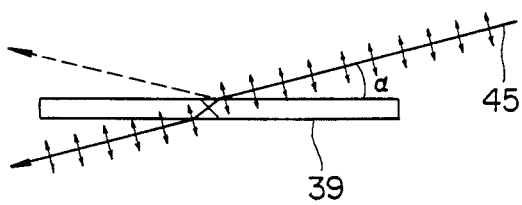
FIG. 9B
FIG. 10
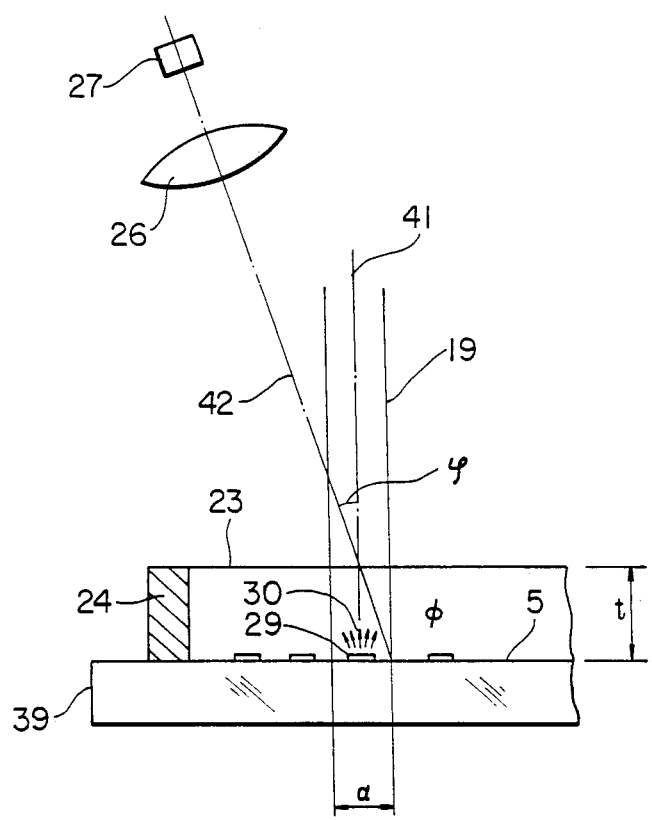

EXPOSURE APPARATUS WITH FOREIGN PARTICLE DETECTOR

BACKGROUND OF THE INVENTION

This invention relates to an exposure apparatus which carries a substrate such as a reticle or a photomask and projects a circuit pattern formed on the substrate upon a wafer, whereby the wafer is exposed to light by utilizing a projection lens or a reflection mirror.

For example, U.S. Pat. Nos. 4,153,371 and 4,362,389 disclose a reduction projection exposure apparatus in which when a circuit pattern formed on a substrate such as a reticle or a photomask is transcribed upon a wafer with a reduction ratio and then chips are exposed to light one by one, a pellicle (a member consisting of a metal frame and a transparent thin film of nitrocellulose applied to the metal frame) adapted to prevent deposition of foreign particles on foreign matter is installed on the substrate in order to prevent the substrate from being deposited with foreign particles. In principle, the substrate mounted with the foreign particle deposition preventive film can prevent deposition of additional foreign particles thereto. The foreign particle deposition preventive film is spaced apart from the surface of the substrate and therefore, even in the presence of relatively small foreign particles on the foreign particle deposition preventive film, an image of the foreign particles will not be transcribed upon the wafer. Accordingly, when the foreign particle deposition preventive film is used, the process covering cleaning of the substrate and exposure of the wafer is carried out as follows.

A substrate is first cleaned and the presence or absence of foreign particles such as dust on a pattern surface and a non-pattern surface of the substrate is examined. If no foreign particle such as dust is found, a foreign particle deposition preventive film is mounted to the substrate by using a suitable tool to cover the entire substrate surface inclusive of the pattern surface. The substrate with the foreign particle deposition preventive film, hereinafter referred to as a substrate assembly, is also checked for the presence or absence of foreign particles on the surface of the assembly according to a method described in Japanese Patent Unexamined Publication No. 59-82727. If no foreign particle is found, the substrate assembly is set in a cassette and the cassette is fed to a reduction exposure apparatus, followed by an exposure process.

Thanks to the foreign particle deposition preventive film, a foreign particle of less than 20 to 30 $\mu$m in size deposited on the surface of the pellicle or film can be considered to be negligible and yield of production of chips can be improved.

However, since probability of foreign particle deposition is in reverse proportion to squared size of a foreign particle, probability of deposition of a foreign particle being of more than 20 to 30 $\mu$m size can not be neglected completely. Further, in the exposure apparatus, there is pressumably a great possibility that a foreign particle is deposited to the foreign particle deposition preventive film in the course that the substrate assembly, typically stored in a magazine, is picked up and then set at a mask table. For these reasons, in order to aim at further improved yield, it is necessary to make an examination of the presence or absence of a relatively large foreign particle on the foreign particle deposition preventive film of the substrate assembly before exposure.

SUMMARY OF THE INVENTION

An object of this invention is to provide an exposure apparatus which can further improve yield for exposure process by checking a substrate assembly for the presence or absence of foreign particles deposited on a foreign particle deposition preventive film of the substrate assembly when a plurality of substrate assemblies (substrates such as reticle or photomasks each mounted with the foreign particle deposition preventive film) are taken out of a magazine one by one and a single one substrate assembly is transported to a mask table which defined an exposure position where the single substrate assembly is set for exposure.

According to this invention, to accomplish the above object, a foreign particle detector for optical detection of foreign particles present on a foreign particle deposition preventive film of a substrate assembly is provided on the way of an automatic transport path between a magazine for storage of a plurality of substrate assemblies standing for reticles or photomasks, respectively removed of foreign particles and mounted with foreign particle deposition preventive films, and a mask table which defines an exposure position where the substrate assembly is set for exposure. A foreign particle detector automatically checks the substrate assembly for the presence or absence of a relatively large foreign particle on the foreign particle deposition preventive film and if the relatively large foreign particle is deposited on the film, it determines that the substrate assembly is defective and the defective substrate assembly is returned to the magazine. This defective substrate assembly is manually taken out of the magazine and removed of the foreign particle by blowing a gas such as nitrogen gas from a nozzle against the assembly. The cleaned assembly is again set in the magazine and subjected to an inspection by the foreign particle detector. If no foreign particle is found, the substrate assembly with the foreign particle deposition preventive film removed of foreign particles is set at the mask table, the photomask and a wafer are aligned with each other, and the wafer is exposed to light through a circuit pattern formed on the substrate.

Especially, the foreign particle detector disposed along the automatic transport path between the magazine and the mask table must be compact. For this requirement of compactness, an inspection light beam incident to the substrate assembly is scanned in one direction by rotating a galvano-mirror and in the other direction by using, also for the scanning purpose, a transport unit adapted to transport the substrate assembly between the magazine and the mask table. To prevent impingement of a positive reflection light beam from the foreign particle deposition preventive film or mask upon a detector optical system, a coherent light beam is obliquely irradiated on the foreign particle deposition preventive film. Further, to prevent impingement of a light beam transmitting through the mask upon the detector optical system, an S-polarized light beam, which is oscillating in a direction parallel to the mask surface, is irradiated on the foreign particle deposition preventive film. Moreover, in order to prevent a light beam reflected at the surface of the mask circuit pattern from being focused on a linear image sensor, a focusing lens and the linear image sensor are both obliquely disposed at an angle of $\phi$ with respect to the vertical plane. Furthermore, a light beam reflected at the upper surface of the frame carrying the foreign particle deposition preventive film is focused on an area outside a detection area of the linear image sensor so as not to be detected by the linear image sensor.

BRIEF DESCRIPTION OF THE DRAWINGS

FIG. 9A is a diagram illustrating a reflection status of an S-polarized wave at the surface of a substrate;

FIG. 9B is a diagram illustrating a reflection status of a P-polarized wave at the substrate surface;

FIGS. 10 and 11 are diagrams for explaining desirable setting states of the optical axis of a scattered light detector system which are suitable for preventing undesired scattered lights.

DESCRIPTION OF THE PREFERRED EMBODIMENTS

Figure 1:
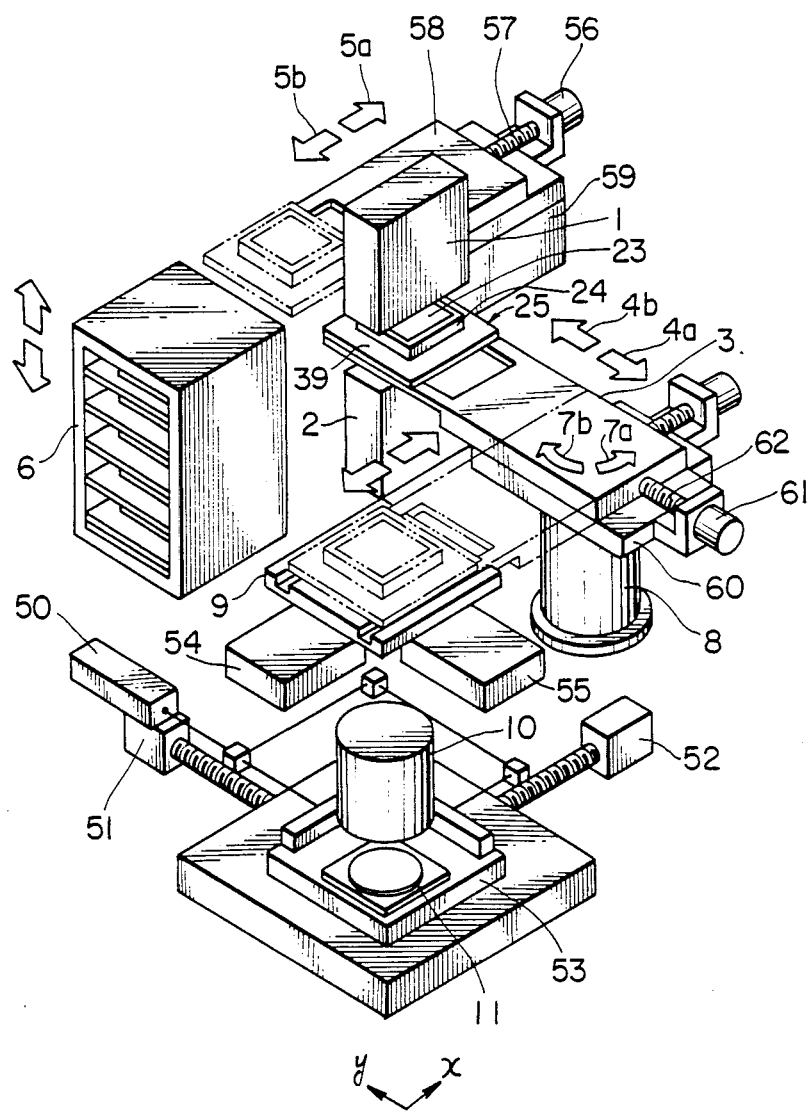
FIGS. 1 and 2 are perspective views showing an exposure apparatus according to an embodiment of the invention.
Figure 2:
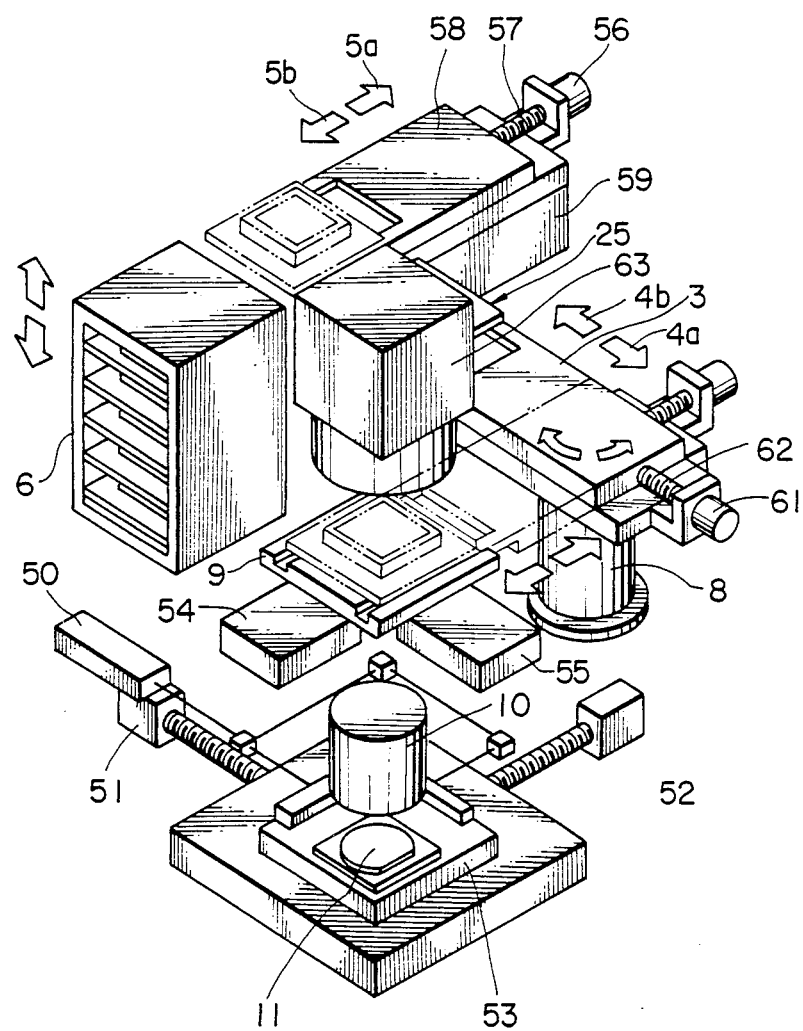

FIGS. 1 and 2 show a preferred embodiment of an exposure apparatus according to the invention, particularly, in the form of a reduction projection exposure apparatus equipped with a foreign particle detector for detection of foreign particles present on a foreign particle deposition preventive film. Referring to FIGS. 1 and 2, a number of substrate assemblies 25 set in cassettes are stored in a magazine 6 provided for the exposure apparatus. Each of the substrate assemblies has a substrate 39 such as a reticle or a photomask and foreign particle deposition preventive films 23 applied on frames 24 mounted to the opposite surfaces of the substrate 39.

When performing exposure, a desired substrate assembly 25 (a substrate 39 mounted with a foreign particle deposition preventive film) is selected from the plurality of substrate assemblies set in cassettes and stored in the magazine 6, and transported by means of a transport unit 3 to a mask table 9 which is situated at an exposure position. The substrate assembly is set to the exposure position by means of a positioning means (not shown) described in U.S. Pat. No. 4,153,371 mentioned previously. The position of a wafer table 53 is measured with a laser type measuring machine 50 and a wafer 11 is moved stepwise and repetitiously at predetermined intervals in x and y directions by means of x and y feed mechanisms 51 and 52. The substrate 39 and the wafer 11 are then aligned with each other by means of optical alignment systems 54 and 55, described in U.S. Pat. Nos. 4,153,371 and 4,362,389 or U.S. patent Application Ser. No. 684,292, and an x, y and $\theta$ (rotation) fine adjustment mechanism (not shown). Subsequently, the circuit pattern formed on the substrate 39 is exposed with a light beam emitted from an exposure light source 63 on the wafer 11. After the circuit pattern formed on the single substrate 39 has been transcripted by exposure on a number of wafers 11 in a similar manner, the substrate assembly 25 is returned from the mask table 9 to the cassette in the magazine 6 by means of the transport unit 3. When it is desired to transcript another circuit pattern on wafers 11, another substrate assembly 25 is taken out of a cassette in the magazine 6 and set to the mask table 9, and an exposure process is carried out in the same manner as described previously.

To describe the above operations in greater detail, the cassettes in the magazine 6 are moved up and down at a pitch of one cassette by means of an elevator (not shown), and a substrate assembly 25 is taken out of a cassette in a direction of arrow 5a by means of a fork 58 which is moved on a base 59 by a feed screw 57 driven by a motor 56. Subsequently, this substrate assembly is moved in a direction of arrow 4a by means of the transport unit 3 in the form of a transport arm which is moved on a rotary base 60 by a feed screw 62 driven by a motor 61. Foreign particles present on the foreign particle deposition preventive films 23 mounted to the opposite surfaces of the substrate 39 are examined with an upper foreign particle detector unit 1 disposed above the transport arm 3 and a lower foreign particle detector unit 2 disposed below the transport arm 3. In the event that a foreign particle of more than 20 to 30 $\mu$m in size, for example, is present on one or both of the foreign particle deposition preventive films 23 of the substrate assembly 25, the motors 61 and 56 are energized to return that substrate assembly to the corresponding cassette in the magazine 6. Since in this case no substrate assembly 25 is located or set at the mask table 9, a waiting condition for exposure is left intact. Then, the operator recognizes that the foreign particle is deposited on one or both of the foreign particle deposition preventive films 23 of the substrate assembly 25, and removes this substrate assembly 25 together with its cassette from the magazine 6. The foreign particle is then removed by blowing a gas such as nitrogen gas and the cleaned substrate assembly along with the cassette is again stored in the magazine 6.

In the absence of foreign particles, on the other hand, the transport arm 3 together with the rotary base 60 is rotated counterclockwise as indicated by arrow 7a so that a substrate assembly is located at the mask table 9 which defines the exposure position. Subsequently, a light beam emitted from the exposure light source 63 is successively irradiated, through a circuit pattern formed on the substrate and an optical projection system 10 comprised of a reduction projection lens, onto chips on a wafer 11 which is moved stepwise and repetitiously at a pitch of one chip, thereby effecting transcript by exposure of the circuit pattern on the respective chips. When an exposure process is completed using the substrate assembly 25, this assembly 25 is returned from the mask table 9 to the corresponding cassette in the magazine 6.

Figure 3:
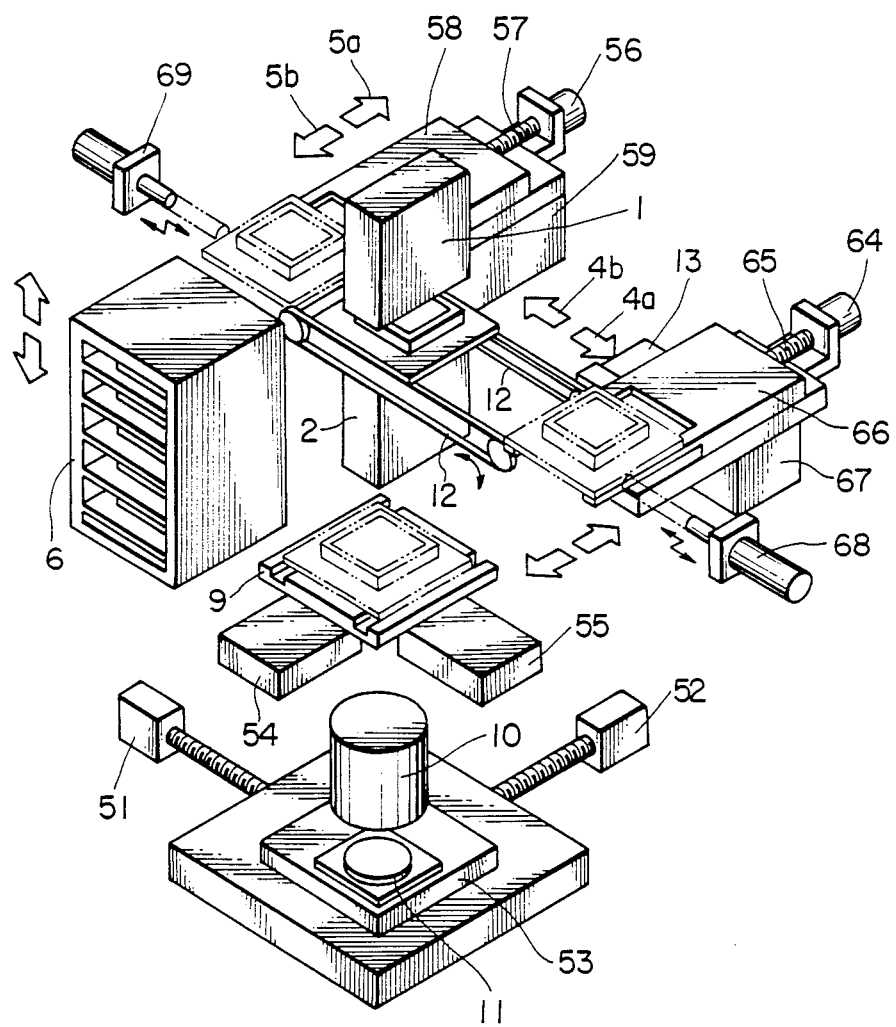
FIG. 3 is a perspective view showing an exposure apparatus according to another embodiment of the invention.

FIG. 3 shows a second embodiment of the invention. In this embodiment, a substrate assembly 25 is taken out of a magazine 6 and transported to a mask table 9 by using a transport unit exemplified as a belt mechanism 12 driven by a motor 13, forks 58 and 66 disposed near the opposite ends of the belt mechanism 12 are driven by feed screws 57 and 65 coupled to motors 56 and 64 to move on bases 59 and 67, and pushers 68 and 69 are operated to transfer the substrate assembly 25 from the forks 58 and 66 to the transport unit.

Figure 4:
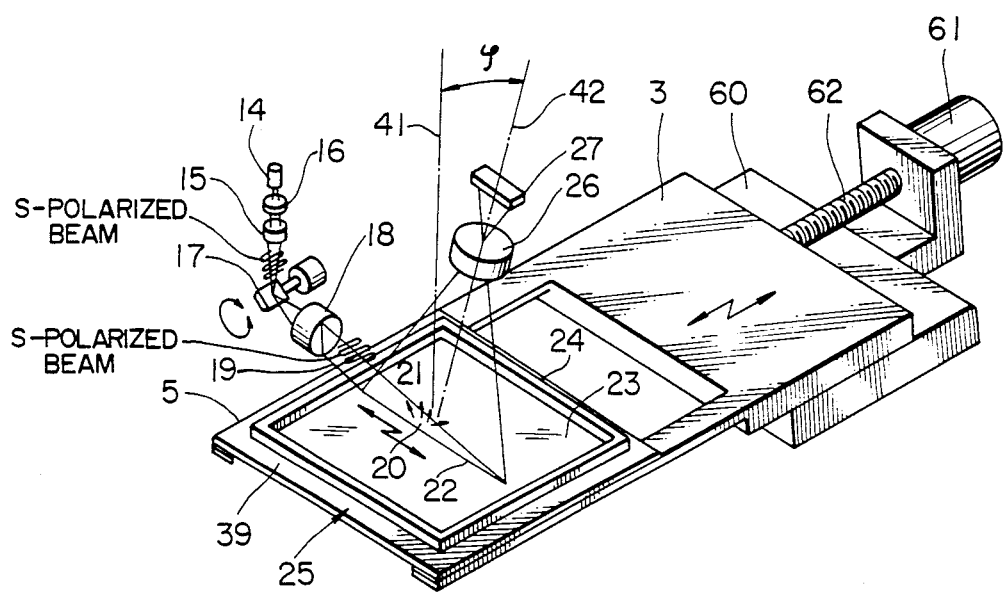
FIG. 4 is a schematic perspective view showing an example of a foreign particle detector according to the invention.
Figure 4:
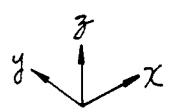

An embodiment of the foreign particle detector unit used in the foregoing embodiments will now be described with reference to FIG. 4. As shown, a laser beam emitted from a laser oscillator 14 is successively passed through a polarizer plate 16 and a condensing lens 15, subjected to total reflection at a galvano-mirror 17 which is rotated for reciprocating rotary oscillation under the application of a triangular waveform signal, and finally passed through a collimator lens 18 so as to be obliquely irradiated on the surface of the foreign particle deposition preventive film 23, forming a laser spot thereon. In this case, the galvano-mirror 17 is driven by the electric signal of a triangular waveform to make a rotary oscillation at a constant period and consequently, the laser spot is scanned to reciprocate on the surface of the foreign particle deposition preventive film 23 at a constant speed in y direction, thereby producing a linear scanning line 22. The galvano-mirror may be replaced with a polygonal mirror.

A detector for detecting a scattered light 21 from a foreign particle 20 comprises an image forming lens 26, a light shield plate (not shown), and a selfscan storage type photoelectric conversion element 27 comprised of a one-dimensional linear sensor such as a CCD or a photodiode array. The detector is so disposed as to obliquely view the scanning line 22 of the laser spot. In other words, an image of the scanning line 22 of the laser spot which linearly scans on the surface of the foreign particle deposition preventive film 23 is focused on the photoelectric conversion element 27 by means of the image forming lens 26. Accordingly, when the laser spot is scanned over the entire surface of the foreign particle deposition preventive film 23 by effecting the linear scanning and by moving the transport arm 3 with the motor 61 and feed screw 62 to feed the substrate assembly 25 at a constant speed in x direction, in the presence of a foreign particle 20 on the scanning line 22, intensity of scattered light 21 from the foreign particle 20 is accummulated and detected at the photoelectric conversion element 27.

Figure 5:
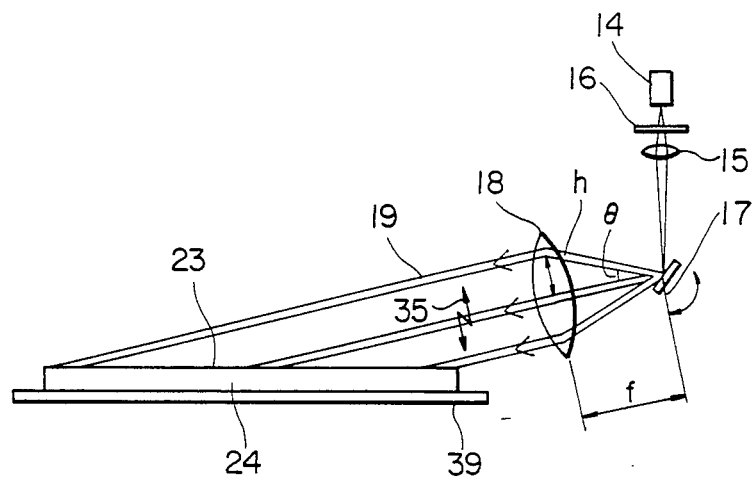
FIG. 5 is a diagram for explaining the operation of a laser beam in a radiation system used in the detector of FIG. 4.

To describe the laser beam irradiation system in greater detail, reference should be made to FIG. 5. A laser beam emitted from the laser oscillator 14 is passed through the polarizer plate 16 (in case where a polarized laser such as a semiconductor laser is used, the polarizer plate is unnecessary), and thereafter focused on the surface of the galvano-mirror 17 by means of the condenser lens 15. The focused beam undergoes total reflection at the surface of the galvano-mirror 17 to reach the collimator lens 18. Since the collimator lens 18 is so arranged that its focal point is located at the rotation center axis of the galvano-mirror 17, the laser beam transmitting through the collimator lens 18 becomes a collimated beam or laser spot 19. This collimated beam is oscillated to reciprocate in directions designated at 35 in FIG. 5 in accordance with the rotary oscillation of the galvano-mirror 17 and as a result, it is linearly scanned to reciprocate on the surface of the foreign particle deposition preventive film 23. Where the focal length of the collimator lens 18 is f, the angle of deflection of the laser beam is $\theta$, and the amount of scanning of the laser spot is h, the scanning amount h is indicated as follows:

$$h = f \cdot \tan\theta \qquad (1)$$

$$\approx f \cdot \theta \ (\tan\theta \approx \theta \text{ for a small } \theta)$$

When the galvano-mirror 17 is rotated at a constant speed, the laser spot is reciprocated at a constant speed on the surface of the foreign particle deposition preventive film 23.

Figure 6:
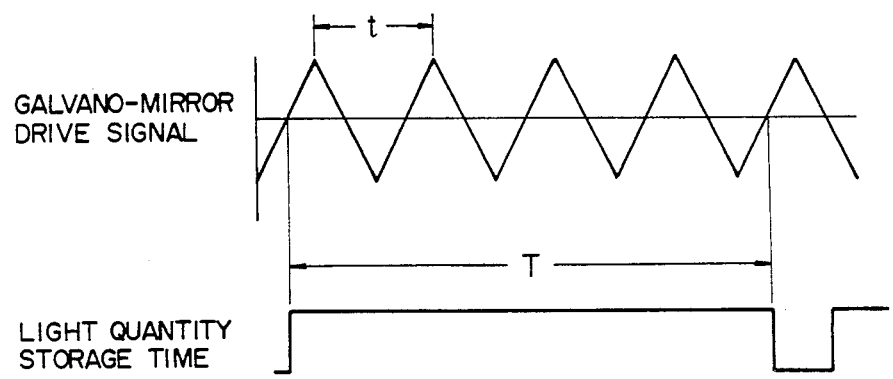
FIG. 6 is a time chart for explaining the relation between a drive signal of a galvano-mirror and a light quantity storage time of a photoelectric element in the detector of FIG. 4.

FIG. 6 illustrates a triangular wave signal for driving the galvano-mirror 17 and a light quantity storage time for a single one photoelectric conversion element 27.

Figure 7:
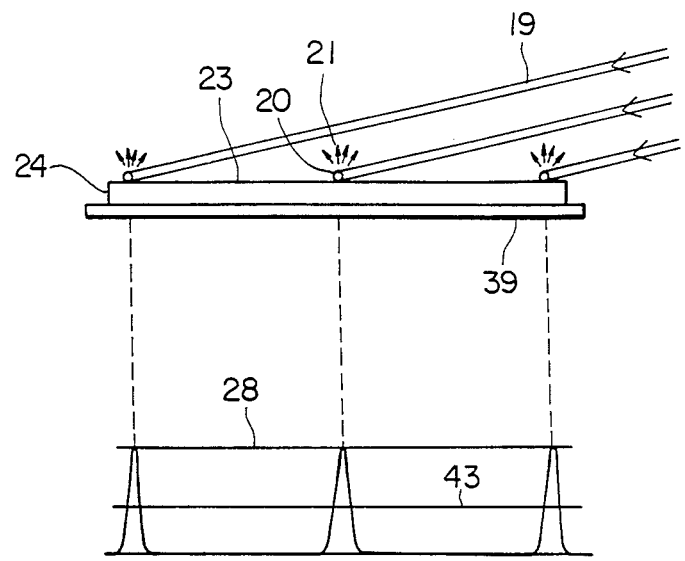
FIG. 7 is a diagram for explaining foreign particle detecting operations in accordance with the invention.

As will be seen from FIG. 6, the photoelectric conversion element 27 has a scanning time T (required for all the sensors of the element to be scanned to deliver an output signal) which is set to be synchronous with a period t of the galvano-mirror, amounting to integer times the period t, and as a result the quantities of light to be stored in the photoelectric conversion element can be increased. In addition, scanning conditions are identical for all the positions to be scanned. For these reasons, as shown in FIG. 7, intensity of scattered light from a foreign particle present near the center on the surface of the foreign particle deposition preventive film 23 becomes equal to that from a foreign particle present at either end, thus providing a substantially uniform scattered light intensity distribution 28. This eliminates the conversional necessity of changing the threshold level in accordance with positions to be scanned and permits the use of a single constant threshold level 43 for ensuring stable detection of foreign particles even when the foreign particle deposition preventive film 23 moves vertically.

Figure 8:
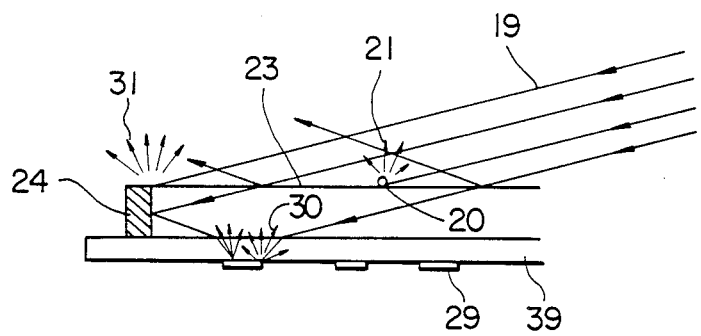
FIG. 8 shows various scattered light beams from portions other than foreign particles.
Figure 11:
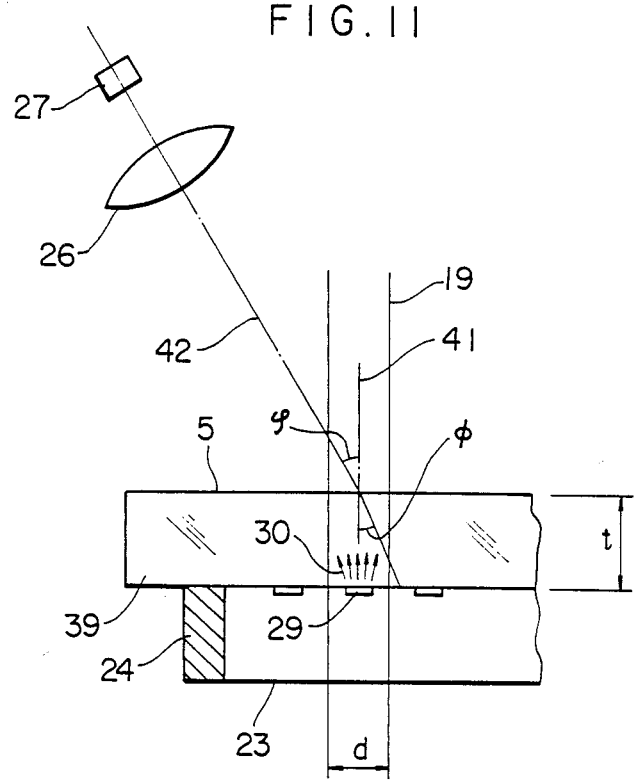
Figure 12:
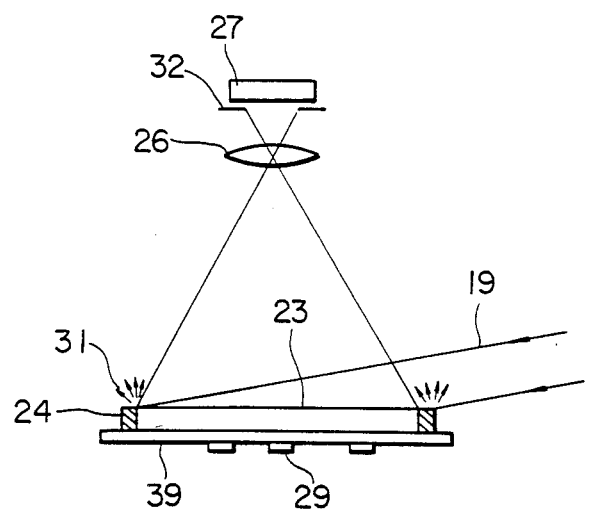
FIG. 12 is a diagram showing a desirable construction of the scattered light detector system which can also prevent detection of undesired scattered lights.

FIG. 8 illustrates other factors than the foreign particle which lead to generation of scattered light. Scattered light liable to be erroneously detected as the scattered light 21 from the foreign particle 20 conceivably involves a scattered light 31 from the frame 24 to which the foreign particle deposition preventive film 23 is applied, and a scattered light 30 caused by impingement of a light beam transmitting through the film 23 upon a pattern 29 formed on the surface 5 of the glass substrate 39. Incidentally, when a light beam such as a laser beam is obliquely irradiated on a transparent material such as a glass substrate as shown in FIGS. 9A and 9B, it is of general nature that, though dependent upon incident angle $\alpha$, a wave whose electric field plane oscillates in a direction parallel to the substrate surface 5 (horizontal direction), that is, a so-called S-polarized wave 44 is predominant in reflection component and conversely, a wave whose electric field plane oscillates in a direction substantially vertical to the substrate surface 5, that is, a so-called P-polarized wave 45 is predominant in transmission component. This fact teaches that, for the purpose of minimizing the influence of the scattered light from the pattern 29 formed on the substrate surface 5, the polarizer plate 16 is preferably used to irradiate the S-polarized wave on the foreign particle deposition preventive film 23 with the result that the light beam transmitting through the film 23 can be minimized. However, a scattered light will be generated from the pattern 29 under irradiation of a very small amount of laser beams passing through the foreign particle deposition preventive film 23. Therefore, as shown in FIGS. 4, 10 and 11, it is preferable that the optical axis 42 of the scattered light detection system be obliquely set, making an angle $\phi$ to a normal 41 of the substrate surface 5, so as to prevent the detection system from viewing a portion of the pattern 29 from which the scattered light 30 is generated. In particular, FIG. 10 shows how the scattered light 30 is generated from the pattern 29 when the surface of the foreign particle deposition preventive film 23 is examined, and FIG. 11 shows how the scattered light 30 is generated from the pattern 29 when the surface of a relatively thick glass substrate 39 having the same function as the foreign particle deposition preventive film 23 is examined. In these figures, d represents the diameter of the irradiated laser beam, t the thickness of the glass substrate 39 or of the frame 24 to which the foreign particle deposition preventive film 23 is applied, and $\Phi$ an angle of refraction for the incident angle $\phi$.

The optical axis 42 for viewing of the detection system passes through the substrate surface 5 or the surface of the foreign particle deposition preventive film 23 and then undergoes refraction or runs straighforward to cross the pattern formation surface on the glass substrate 39. Accordingly, in the examples of FIGS. 10 and 11, the condition for permitting the scattered light detection system to be unable to detect the scattered light 30 from the pattern 29 is such that the irradiation beam does not fall within the beam diameter d. To meet this condition, $\phi$ must be set so as to satisfy the following formula:

$$\phi \geq \sin^{-1}\{n \sin(\tan^{-1} d/2t)\} \ldots \quad (2)$$

where n is a refractive index.

Practically, however, a satisfactory value of $\phi$ slightly deviates from that obtained from the above formula under the influence of such factors as aberrations of the image forming lens 26, and $\phi$ is set within a range of approximately more than 0° to less than 20°.

On the other hand, the scattered light 31 generated from the frame 24 to which the foreign particle deposition preventive film 23 is applied can be shielded by a light shielding unit 32 additionally provided at an image forming position of the photoelectric conversion element 27. Especially, when the light shielding unit is properly disposed near the image forming lens 26, it is possible to permit the photoelectric conversion element 27 to be unable to detect the scattered light 31 from the frame 24.

In the foregoing embodiment, the foreign particle detector is located on the way of the transport path of the substrate but it may alternatively be disposed above the mask table 9. However, it is practically difficult to reserve a space for the disposition of the foreign particle detector above the mask table since the optical systems 54 and 55 for alignment of the mask and wafer must be disposed near and above the mask table 9. In an alternative, adjacent the foreign particle detection units 1 and 2, such a unit as the nozzle which ejects a gas such as a nitrogen (N$_2$) gas for removal of foreign particles from the foreign particle deposition preventive film may be provided.

Obviously, the application of this invention is not limited to the projection type exposure apparatus utilizing the projection lens but the invention is also applicable to a 1:1 reflection type projection exposure apparatus utilizing a reflection mirror.

In summary, by using the foreign particle detector disposed along the transport path through which the substrate assembly 25 taken out of the magazine 6 is automatically transported to above the mask table 9, it is possible to examine the presence or absence of foreign particles deposited on the foreign particle deposition preventive film in the course that the substrate assembly is taking a position which is most close to the exposure position, thereby greatly contributing to improving the yield.

As described above, according to the invention, the foreign particle present on the foreign particle deposition preventive film can be inspected with the simplified and compact foreign particle detector immediately before the exposure process and hence the yield for the exposure process can be greatly inproved in the projection type exposure apparatus or reflection type exposure apparatus used in combination with the foreign particle deposition preventive film.

We claim:

1. An exposure apparatus comprising:

a magazine for storing a plurality of substrate assemblied each including a substrate such a a recticle or photomask used for exposure and frames, mounted to the opposite surfaces of said substrate, to which foreign particle deposition preventive films are applied;

transport means for taking a substrate assembly out of said magazine, transporting the taken out substrate from said magazine to a mask table disposed at an exposure position and setting that substrate assembly at said mask table;

foreign particle detection means, provided near said transport means, for optically detecting foreign particles present on said foreign particle deposition preventive films of said surface assembly;

means for aligning said substrate assembly set at said mask table and a wafer; and means for irradiating a light beam on said substrate assembly aligned relative to said wafer and projecting a circuit pattern formed on said substrate upon said wafer through a projection optical system to expose said wafer to the light beam through said circuit pattern;

wherein said foreign particle detection means comprises light beam irradiation means for obliquely irradiating a collimated light beam on said foreign particle deposition preventive film in a direction vertical to a transport direction of said transport means to linearly scan the collimated light beam on said film, means for foreign particle deposition preventive film in the transport direction by moving said transport means, and imaging means, comprised of an image forming lens and photoelectric conversion means, for detecting a refection beam generated by scanning said foreign particle deposition preventive film with said collimated light beam, and photoelectric onversion means, for detecting a 2. An exposure apparatus according to claim 1 wherein said light beam irradiation means comprises an optical system comprised of a mirror which is rotatable to linearly scan the collimated light beam.

3. An exposure apparatus according to claim 2 wherein said light beam irradiation means comprises a laser oscillator for emitting a laser beam, a condenser lens for condensing the laser beam from said laser oscillator onto said mirror, and a collimator lens for converting the laser beam scanned by said optical system into the collimated laser beam.

4. An exposure apparatus according to claim 1 wherein said light beam irradiation means comprises means for irradiating on said foreign particle deposition preventive film an S-polarized beam which oscillates in a direction parallel to said film.

5. An exposure apparatus according to claim 4 wherein said light beam irradiation means comprises a laser oscillator for emitting a laser beam, a condenser lens for condensing the laser beam from said laser oscillator onto said mirror, and a collimator lens for converting the laser beam scanned by said optical system into the collimated laser beam.

6. An exposure apparatus according to claim 1 wherein said imaging means comprises said image forming lens and photoelectric conversion means both aligned on an optical axis which is inclined by an angle $\phi$ relative to a plane which is vertical to said foreign particle deposition preventive film and which crosses the direction of linear scanning by said light beam irradiation means.

7. An exposure apparatus according to claim 6 wherein said photoelectric conversion means comprises a linear image sensor including sensor elements arrayed in the direction of linear scanning by said light beam irradiation means.

8. An exposure apparatus according to claim 1 further comprising light shield means for shielding a reflection beam from the surface of said frame to which said foreign particle deposition preventive film is applied to permit said photoelectric conversion means to be unable to receive that reflection beam.

9. An exposure apparatus according to claim 1 wherein said foreign particle detection means is disposed near said transport means which is provided between means for taking said substrate assembly out of said magazine and means for setting said substrate assembly at said mask table.

* * * * *

UNITED STATES PATENT AND TRADEMARK OFFICE
CERTIFICATE OF CORRECTION

PATENT NO. : 4,676,637
DATED : June 30, 1987
INVENTOR(S) : UTO, et al

It is certified that error appears in the above-identified patent and that said Letters Patent is hereby corrected as shown below:

Column 8,

Claim 1, line 2, delete "assem-";
line 3, delete "blied" and insert --assemblies--;
line 9, after "substrate" insert --assembly--;
line 16, delete "surface" and insert --substrate--;
line 31, after "for" insert --further scanning said collimated light beam on said--;
line 38, delete "and photoelectric onversion means, for de-";
line 39, delete "detecting a".

Signed and Sealed this

Second Day of January, 1996

Attest:

BRUCE LEHMAN

Attesting Officer

Commissioner of Patents and Trademarks